(12) United States Patent
Fukushima et al.

(10) Patent No.: US 7,636,152 B2
(45) Date of Patent: Dec. 22, 2009

(54) CELL COUNTING BOARD

(75) Inventors: Hisashi Fukushima, Hiroshima (JP); Kazuki Sugiyama, Kyoto (JP)

(73) Assignee: Onecell Inc., Hiroshima (JP)

( * ) Notice: Subject to any disclaimer, the term of this patent is extended or adjusted under 35 U.S.C. 154(b) by 0 days.

(21) Appl. No.: 12/300,269

(22) PCT Filed: May 9, 2007

(86) PCT No.: PCT/JP2007/059583

§ 371 (c)(1),
(2), (4) Date: Nov. 10, 2008

(87) PCT Pub. No.: WO2007/132707

PCT Pub. Date: Nov. 22, 2007

(65) Prior Publication Data

US 2009/0073418 A1    Mar. 19, 2009

(30) Foreign Application Priority Data

May 11, 2006    (JP) .............................. 2006-132430

(51) Int. Cl.
*G01N 33/48*    (2006.01)
(52) U.S. Cl. ...................................................... 356/39
(58) Field of Classification Search ................... 356/39
See application file for complete search history.

(56) References Cited

U.S. PATENT DOCUMENTS 5,349,436 A * 9/1994 Fisch ......................... 356/246

FOREIGN PATENT DOCUMENTS

JP    S34-012823    8/1959
JP    H11-160310 A    6/1999

* cited by examiner

*Primary Examiner*—Roy Punnoose
(74) *Attorney, Agent, or Firm*—Global IP Counselors, LLP (57) ABSTRACT

A disposable cell counting board in which a space formed by a counting board body and an upper plate is fixed in advance, and which does not require assembling by a cell counting worker, and which can be mass-produced at low costs, is provided.

The cell counting board comprises a main body and a cover plate attached to the main body. The main body comprises a planar lands positioned at a lower position by a predetermined distance with respect to the top face of the other part than the lands, a counting sections provided at the lands, and four projection sections in the vicinity of the lands for positioning and fixing the cover plate above the lands. The cover plate has engagement holes formed at locations corresponding to the projection sections. A space of the predetermined distance, 0.1 mm, is generated between the top face of the lands and the bottom face of the cover plate, when the cover plate is attached to the main body by engaging each of the projection sections with the corresponding engagement hole.

7 Claims, 12 Drawing Sheets

Prior Art

Fig.12(a)

Prior Art

Fig.12(b)

Prior Art

CELL COUNTING BOARD

TECHNICAL FIELD

The present invention relates to a cell counting board for the purpose of cell counting for research and development in the biological field relating to medicine, pharmacy, agriculture, engineering, science, especially cell biology, cell physiology, biochemistry, molecular biology, hematology, immunology, pharmacology, botany, microbiology, and related fields of industry thereof. In particular, the present invention relates to a cell counting board of disposable type which is discarded after use once.

BACKGROUND ART

Instruments called as a cell counting board or a hemocytometer have been used as an easy method for counting of blood cells, cultured cells, or cells isolated with enzymes, or the like. As shown in a perspective illustration of FIG. 11 as an example, this cell counting board comprises a cell counting board body 70 with a similar size of a microscopic glass slide, and a glass plate 80 with a similar size of a cover glass.

Figure 11:
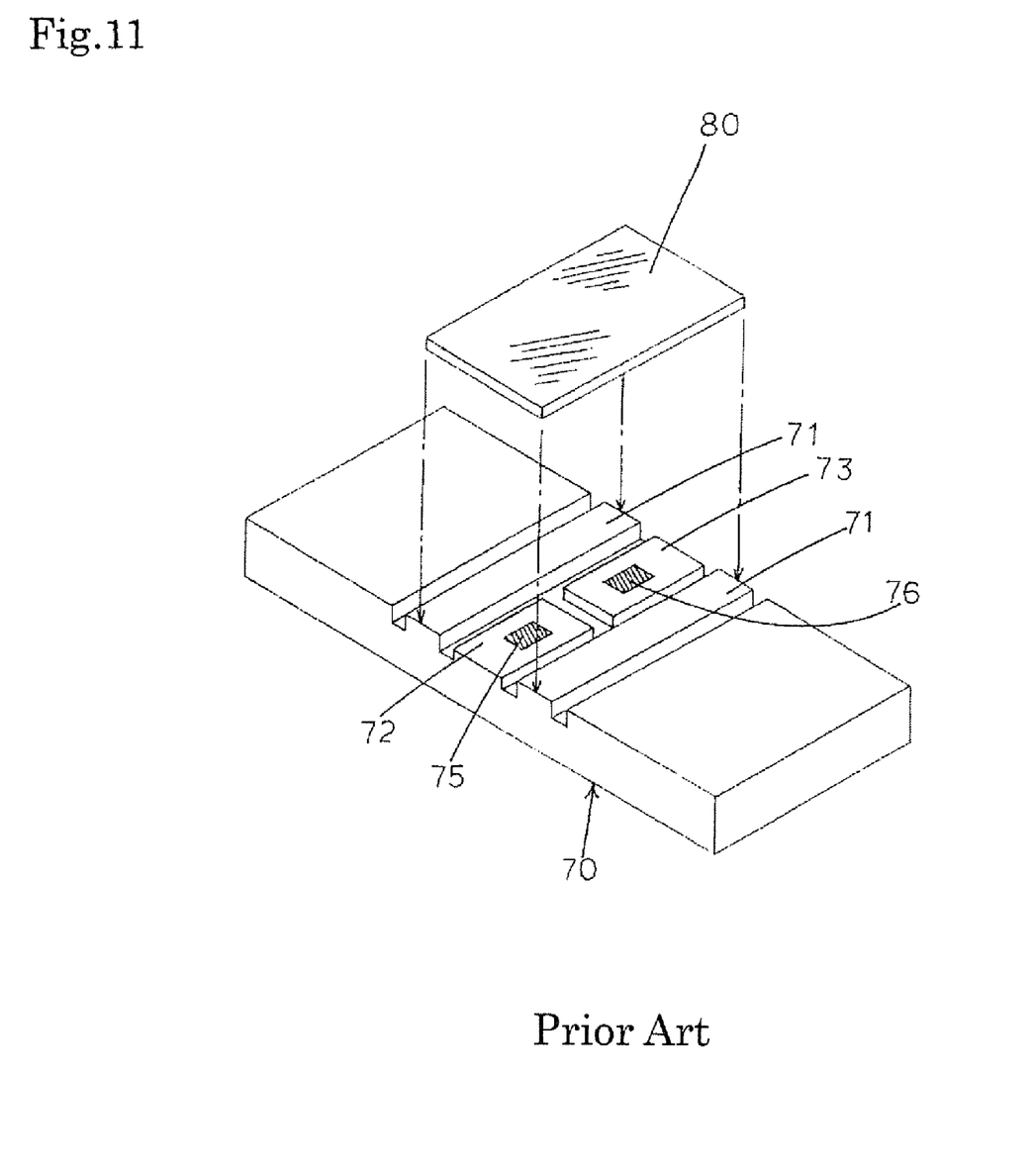
FIG. 11 shows an exploded perspective view of a cell counting board related to a conventional example.

The counting board body 70 has two lands 71, 71, and two lands 72, 73 which are located between the land 71 and the land 71. In the central portion of the lands 72, 73, are provided cell counting sections 75, 76 marked off with a grid pattern. The cell counting sections 75, 76 have a role for easy counting of cells as described later. A pitch difference between the lands 71, 71, and the lands 72, 73 is about 0.1 mm; the planes (top faces) of the lands 72, 73 are positioned at a lower position than the planes (top faces) of the lands 71, 71. The glass plate 80 is mounted above the lands 72, 73 so as to attach the glass plate 80 to the lands 71, 71. The glass plate 80 is adhered and fixed to the counting board body 70 (lands 71, 71) usually by a surface tension of water after getting the peripheral portions of the glass plate 80 wet with water, or getting them moisture with expired gas, and putting the glass plate 80 on the counting board body 70, and subsequently pushing the glass plate 80 with fingers strongly.

Figure 12A:
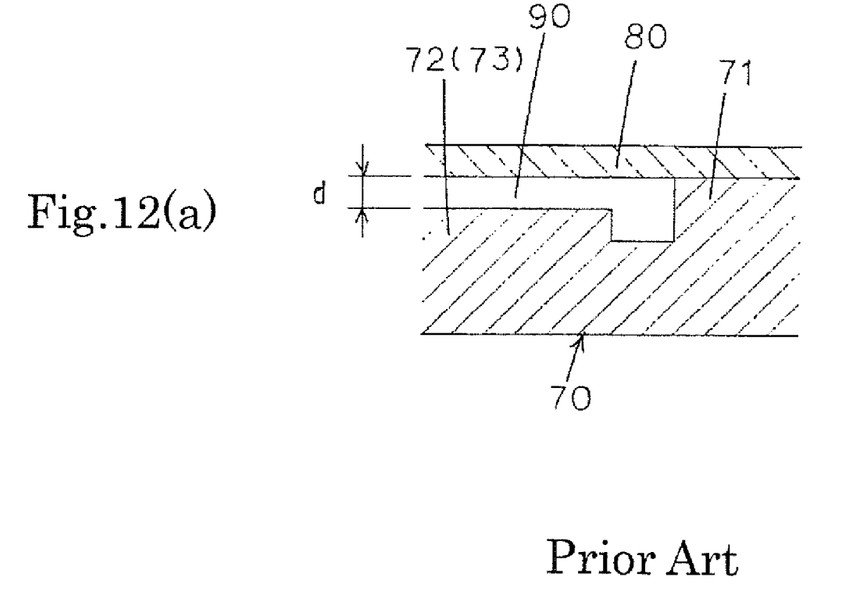
FIG. 12(a) shows an essential part of grossly enlarged sectional view of the cell counting board related to a conventional example.

FIG. 12(a) shows an essential part of grossly enlarged sectional view of the cell counting board 70 attached with the glass plate 80 to the counting board body 70. Because there is a pitch difference between the lands 71, 71, and the lands 72, 73, a space 90 with a constant width (dimension d=0.1 mm) is formed between the plane of the lands 72 (73) and the lower face of the glass plate 80. When the blood diluted or cell suspension is injected into the space 90 with a pipette chip or the like, the liquid fills the space 90 by the surface tension thereof.

On the other hand, the cell counting sections 75, 76 of the cell counting board body 70 are marked off with a grid pattern of thin lines, and the width of the division of the grid pattern is constant. After the cell suspension is injected into the space 90 with a pipette chip or the like, and the liquid fills the space 90 by the surface tension thereof, the cells are observed at the division of the grid pattern, on observation with a microscope or the like. Because the distance of the space at the area of the square part of the division is constant, the rectangular solid with the constant volume is filled with the constant volume of the blood diluted or cell suspension. For example, one assumes the situation where N cells were observed at the area of the square part of the division of 1 mm in width of the cell counting sections 75, 76. In the case of the above space 90 of 0.1 mm in width (d), N cells are present at the rectangular solid with 1 mm×1 mm×0.1 mm. Because 1 mm×1 mm×0.1 mm=0.0001 mL, N cells are present in 0.0001 mL of the injected cell suspension. Therefore, it is easily calculated that the cell suspension injected has the cell density of N×10000/mL.

A definite amount of a blue dye, trypan blue, solution is added to the cell suspension before the injection, the dead cells are stained black-blue dark by intracellular invasion of the blue dye, trypan blue, solution. In contrast, viable cells are not stained black-blue dark, because the viable cells do not allow the intracellular invasion. On this principle, viable cells and dead cells in the cell suspension can be counted separately, by counting the black-blue dark-stained cells and non-stained cells separately.

Conventionally, the material of these cell counting boards has been glass. The cell counting board has been expensive because are needed abrasion works for the purpose of keeping the accurate dimension of the width, and precise works for marking off the accurate lines of the cell counting section 75, 76. Therefore, the cell counting board has been used repeatedly by washing it after use. Expensive glass cell counting boards have been often damaged easily and became unusable by dropping it to the ground. This has been a drawback of the glass cell counting board. In the case where many samples are to be counted for cell numbers, there has been a need for operations where, after counting cells of one sample, the counting board body 70 and the glass plate 80 are washed with water, are washed out the cells and the blue dye, trypan blue, and are wiped off water, and are dried, and subsequently the counting board body 70 and the glass plate 80 are adhered and fixed again. Viable cells die in the blue dye, trypan blue, solution, when they are allowed to stand for 5 minutes. So, the cell counting had to be performed within a few minutes. The above water-washing operations made it difficult to count many samples for a short time. Besides, the operations are troublesome and time-consuming. In the case of research of clinical samples, disposable cell counting boards are in keen demand for the biohazardous handling of infectious bacteria and viruses.

For this purpose, there has been a desire for a disposable cell counting board which is made of plastic resin, and has a space between a counting board body and an upper plate already fixed in advance, and is unnecessary to be assembled by persons dealing with cell counting. A few products for this purpose are known where the counting board body and the upper plate are made of plastic resin and the counting board body and the upper plate are fixed in advance with adhesive (e.g., Patent reference 1).

Figure 12B:
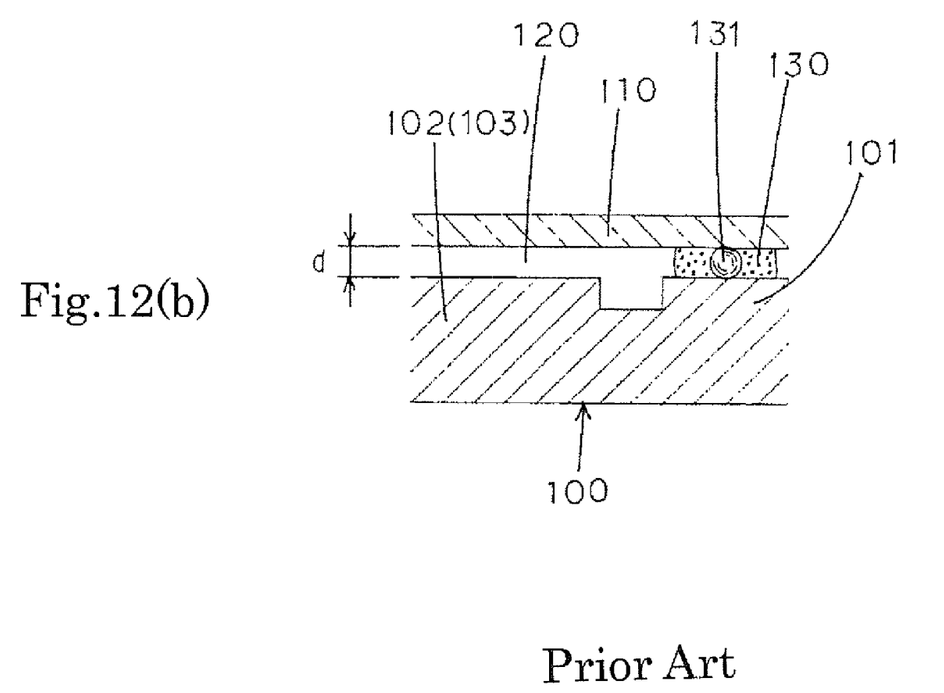
FIG. 12(b) shows an essential part of grossly enlarged sectional view of the cell counting board related to another conventional example.

In the hemocytometer described in this Patent reference 1, as shown in FIG. 12(b), a counting board body 100 and an observation plate 110 are fixed with adhesive 130, and adhesive 130 are mixed with a spacer (spherical particle 131 with a constant particle size) so as to form a clearance 120 with a constant width. This hemocytometer is suitable as a disposable one which can be discarded after use only once.

Patent reference 1: JP-1999-160310-A

DISCLOSURE OF THE INVENTION

Problems to be Solved by the Invention

However, in the case of the hemocytometer described in the above Patent reference 1, the observation plate 110 is needed to be located and fixed with adhesive 130 at the accurate position of the counting board body 100 (lands 101, 102, 103). So the fixation with adhesive 130 takes extremely much trouble, and is not suitable for quality control and retention of the space 120 formed by the observation plate 110 and the land 102 (103). A device for accurate retention of the space 120 is necessary. Furthermore, the fixation with adhesive 130 must be performed for every each hemocytometer, and the fixation takes a cost and unsuitable for mass production.

As to a disposable cell counting board which is generally made of plastic resin and in which space formed by a counting board body and an upper plate is fixed in advance, and which does not require assembling by a cell counting worker, there has been a desire for mass production at low costs for its purposes. To do so, a manufacturing method for a simple fixation of the cell counting body and the upper plate has been desired, in which the fixation is not due to the adhesive technique like the described Patent reference 1 that takes extremely much trouble and unsuitable for quality control and retention of the space.

The present invention has been performed in view of such situation. An object of the present invention includes providing a disposable cell counting board in which a space formed by a counting board body and an upper plate is fixed in advance, and which does not require assembling by a cell counting worker, and can be mass-produced at low costs.

Means for Solving the Problems

To achieve the above object, the cell counting board of the present invention is characterized in that it comprises a main body and a cover plate attached to the main body, wherein the main body comprises a planar land section (land section may be referred to as "land") positioned at a lower position by a predetermined distance with respect to the top face of the main body, a counting section for counting cells provided at the land section, and at least two projection sections for positioning and fixing the cover plate on the land section, the projection section being provided in the vicinity of the land section, the cover plate has engagement holes formed at locations thereof, the location corresponding to the projection section of the main body, and wherein a space of the predetermined distance is generated between the top face of the land section of the main body and the bottom face of the cover plate, when the cover plate is attached to the main body by engaging each of the projection sections of the main body with the corresponding engagement hole of the cover plate.

In the cell counting board, the main body and the cover plate is preferably made of synthetic resin. The synthetic resin which may be used are, for example, styrene group: polystyrene resin and AS (acrylonitrile/styrene) resin; acrylic group: polymethacryl acid resin, acrylonitrile resin; olefin group: polyethylene resin, polypropylene resin; vinyl group: polyvinyl chloride; polycarbonate resin, polyethylene-terephtalate resin, polyarylate resin or blend thereof and the like. These resin may be included, if necessary, any components which make change of characteristics such as hardness, wettability, and the like. In the case of resin with weak hydrophilicity, the surface of the resin may be processed by conductive treatment such as corona discharge and the like, and surface characteristics of wettability and electric charge and the like may be changed so as to let cell suspension inject easily into the counting sections thereof.

Also, the projection sections of the main board are preferably disposed at the positions sandwiching the lands, two projection sections at one side and the other two at the other side, considering the production cost of the main body and the cover plate, and assembly operation characteristics for easiness of attachment of the cover plate to the main body, and accurate positioning and the like Furthermore, the projection sections of the main board are preferably rectangular parallelepiped shape having a hook-shaped leading edge section, for the purposes of easiness of attachment and processing characteristics.

Advantage of the Invention

Because the cell counting board of the present invention is composed as explained the above, it has advantages as follows.

(1) The cover plate can be attached to the main body only by engaging the engagement holes of the cover plate to the projection section of the main body. So, assembly operation is easy.
(2) Because a space of the predetermined distance is formed between the top face of the land section of the main body and the bottom face of the cover plate by attachment of the cover plate to the main body, it does not take labor and time for keeping the accuracy of the distance of the space.
(3) Owing to the above (1), and (2), it can be mass-produced at extremely low costs.
(4) It is suitable for disposable from view points of the above (3) and the biohazard and the like.
(5) It has superior characteristics for convenience, because it is a simple structure where the engagement holes of the cover plate are engaged to the projection sections of the main body.
(6) As composed of the claim 2, it has more outstanding advantages (1) through (5).
(7) As composed of the claim 3, the attachment of the cover plate to the main body can be performed more securely and at low costs.
(8) As composed of the claim 4, the attachment of the cover plate to the main body can be realized with a simpler structure.

BRIEF DESCRIPTION OF THE DRAWINGS

FIGS. 10(a), 10(b), and 10(c) show comparison of the results between the cell counting performed using the cell counting board related to the embodiment, and that by conventional methods, and wherein

EXPLANATION OF THE REFERENCES

10(A~E) the main body
12, 13 land
14, 15 counting section
17 ditch
20, 25 projection section
20a, 25a leading edge section
30 cover plate
32 engagement hole
40 space

BEST MODE FOR CARRYING OUT THE INVENTION

Hereinafter, the present invention is described based upon the embodiments.

Figure 1A:
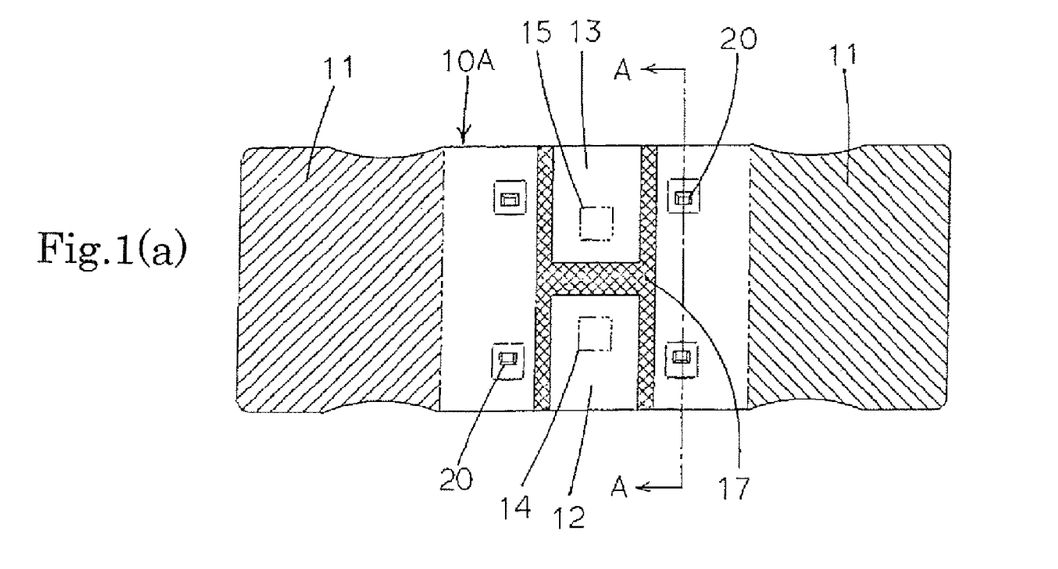
FIG. 1(a) shows a plan view of the main body of the cell counting board related to one embodiment.
Figure 1B:
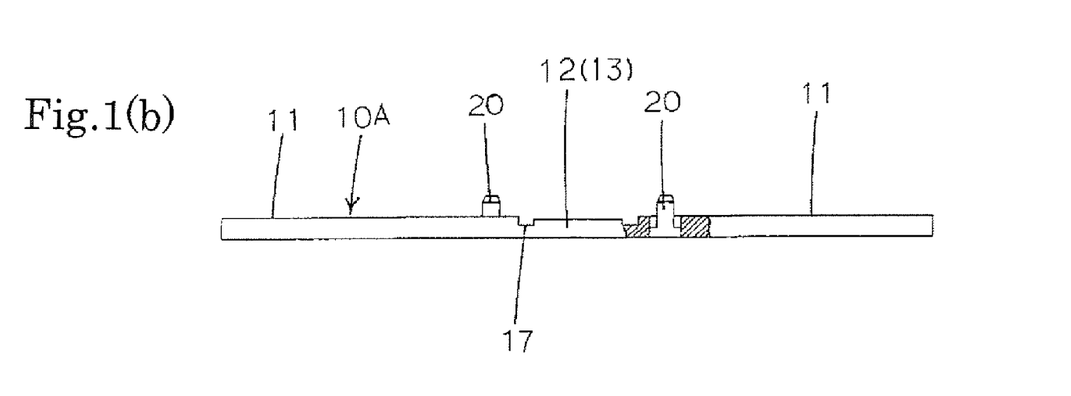
FIG. 1(b) shows its partial broken front view.
Figure 2A:
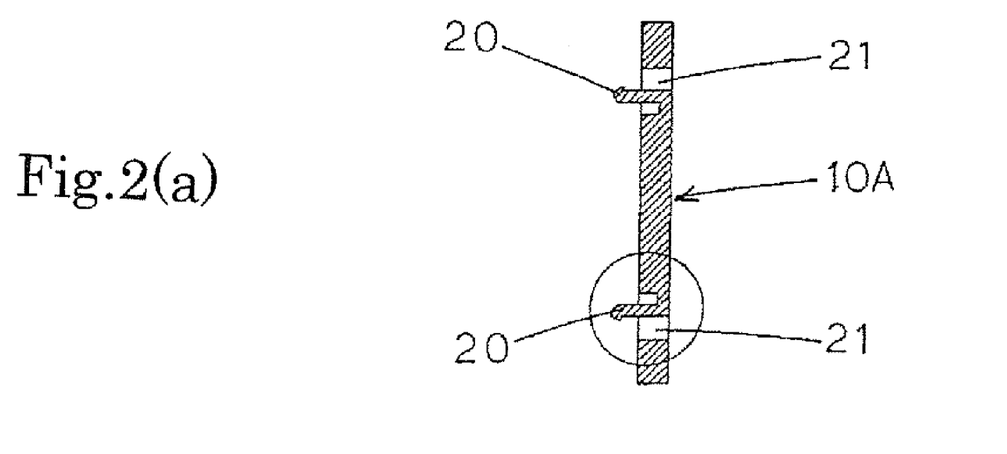
FIG. 2(a) shows a cross-sectional view taken along the line A-A in FIG. 1(a)
Figure 2B:
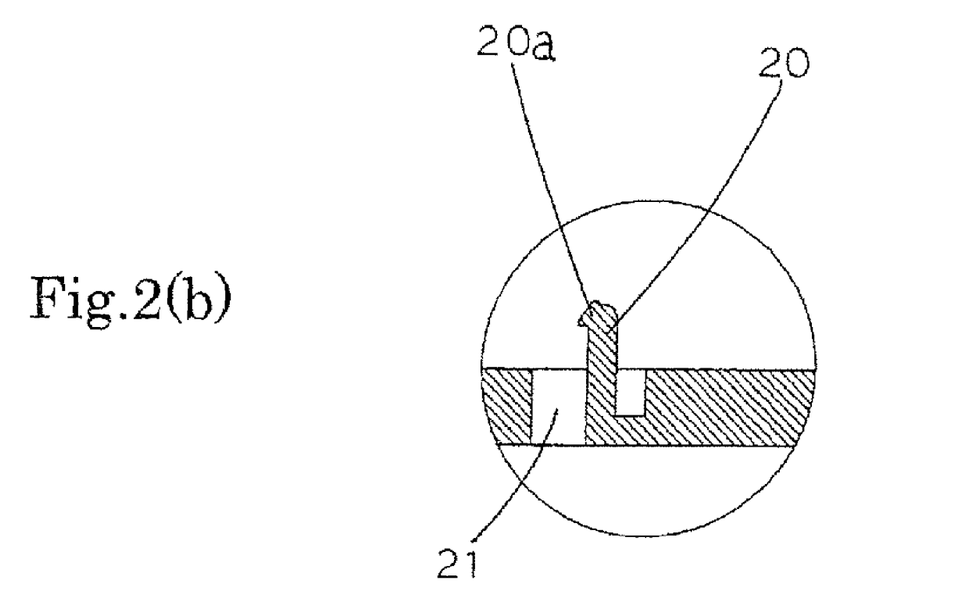
FIG. 2(b) shows an enlarged view of the circular part of FIG. 2(a).

A plan view of the main body of the cell counting board related to one embodiment is shown in FIG. 1(a). A partial broken front view of the main body is shown in FIG. 1(b). A cross-sectional view taken along the line A-A in FIG. 1(a) is shown FIG. 2(a), and an enlarged view of the circular part of the FIG. 2(a) is shown in FIG. 2(b).

The main body 10A is a rectangular object made of synthetic resin (for example polystylene), and two flat lands 12, 13 at the central portion of long distance direction are provided with it. These lands 12, 13 are positioned lower a predetermined distance (about 0.1 mm) than the upper surface of other part 11. There is a pitch difference between the part 11 and the lands 12, 13. Also, counting sections 14, 15 are provided with the lands 12, 13 respectively for cell counting. As described above, these counting sections 14, 15 are, for example, marked off with a grid pattern of thin lines, and the width of the division of the grid pattern is constant. A ditch (mesh pattern part) 17 of a H letter shape is formed around the lands 12, 13 so as to allow the excess liquid to overflow and allow both different sample liquid not to mix in the case of use of different samples at the lands 12, 13. Also, the slanted lines part of the part 11 and the ditch 17 are graining-processed.

As a characteristic in this main body 10A, four projection sections having rectangular parallelepiped shape are disposed at positions sandwiching the lands 12,13, two projection sections at one side and the other two at the other side, in the vicinity of the lands 12, 13 of the part 11, so as to position and fix the cover plate 30 described later on the lands 12, 13. The projection sections 20, as shown in detail in FIG. 2, protrudes erectly from lower side of the quadrangular hole 21 to the upper direction, and the leading edge section 20a is hook-shaped. This projection section 20 has a moderate elasticity.

Figures 3A, 3B:
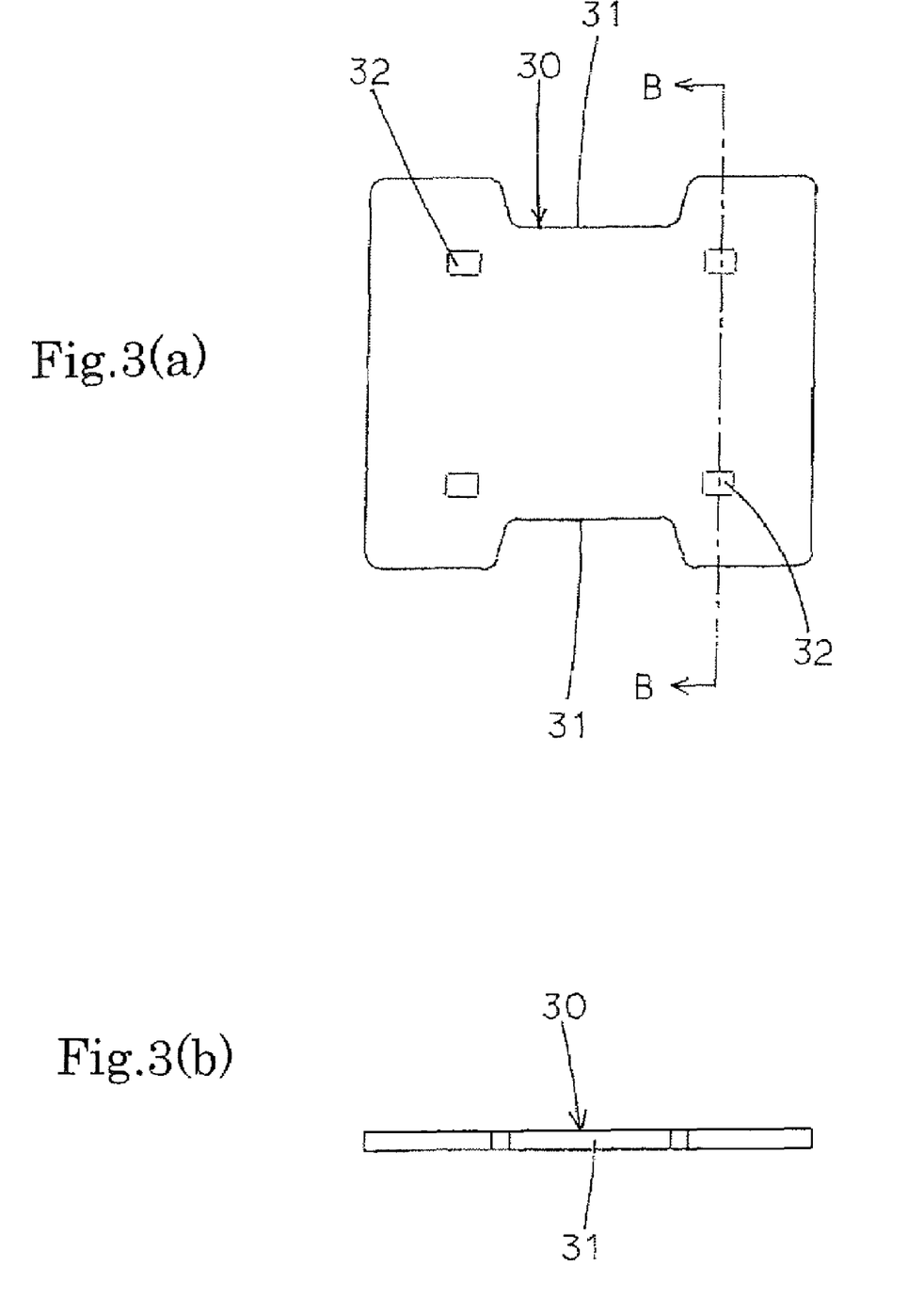
FIG. 3(a) shows a plan view of the cover plate of the cell counting board.
FIG. 3(b) shows its front view.
Figure 4:
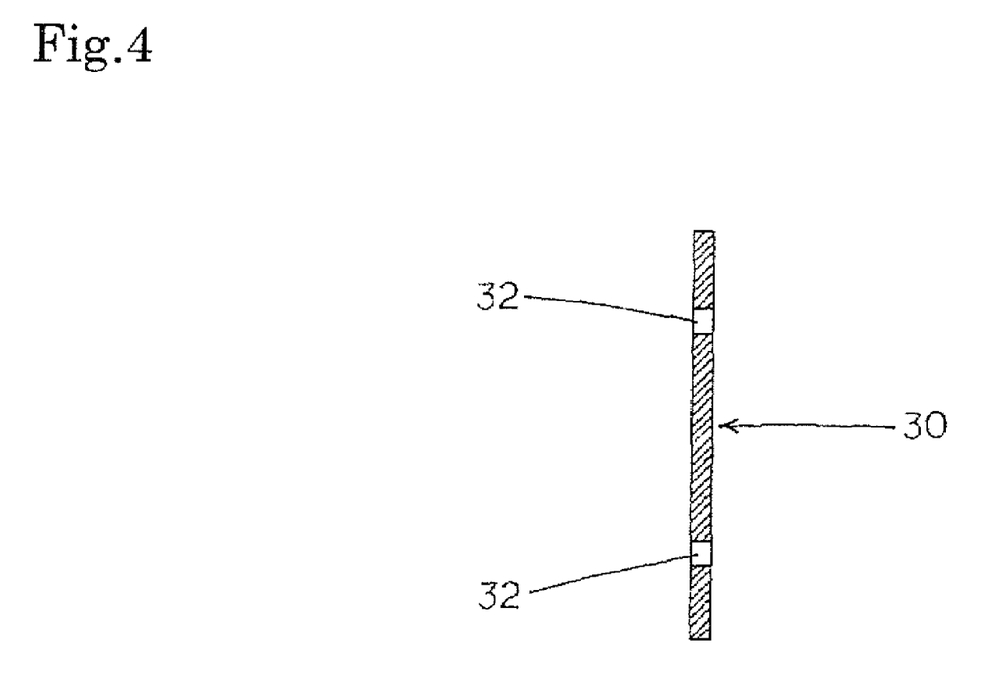
FIG. 4 shows a cross-sectional view taken along the line B-B in FIG. 3(a)

A plan view of the cover plate of the cell counting board is shown in FIG. 3(a), a front view is shown in FIG. 3(b), and a cross-sectional view taken along the line B-B in FIG. 3(a) is shown FIG. 4.

The cover plate 30 is a rectangular object made of synthetic resin (for example polystylene), and have cutout portions 31 corresponding to the lands 12, 13 of the main body 10A, and four quadrangular engagement holes 32 are formed at the positions corresponding to the four projection sections 20 of the main body 10A.

Figure 5A:
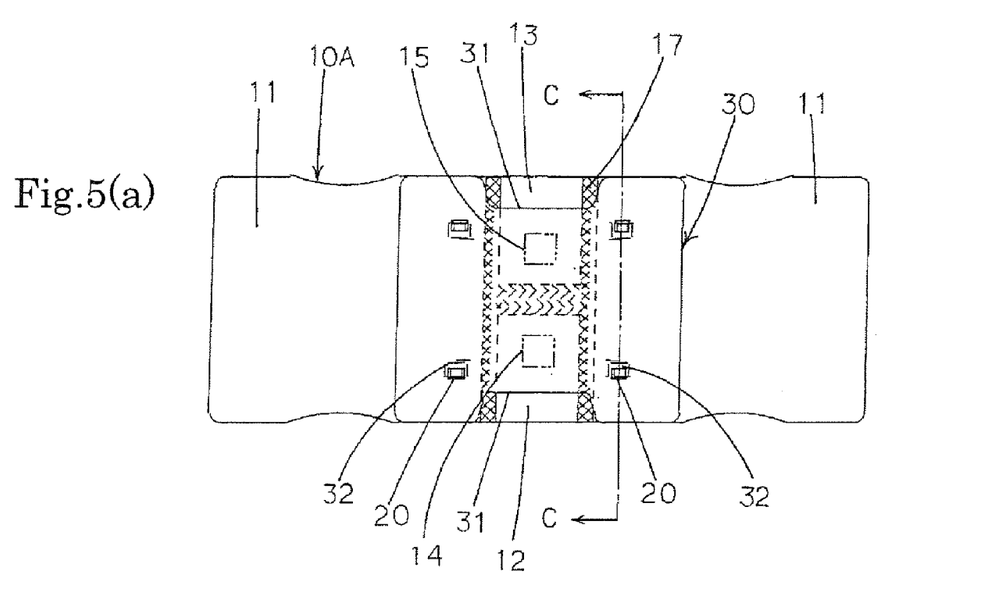
FIG. 5(a) shows a plan view of the cell counting board wherein the cover plate is attached to the main body.
Figure 5B:
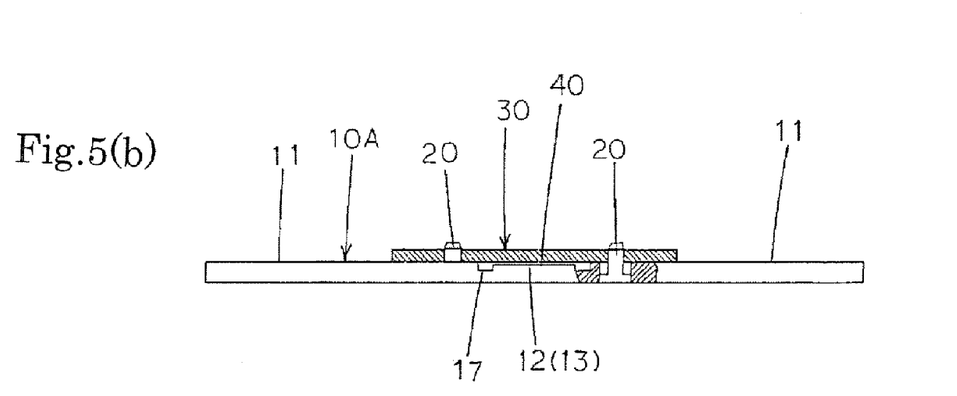
FIG. 5(b) shows its partially broken front view.
Figure 6:
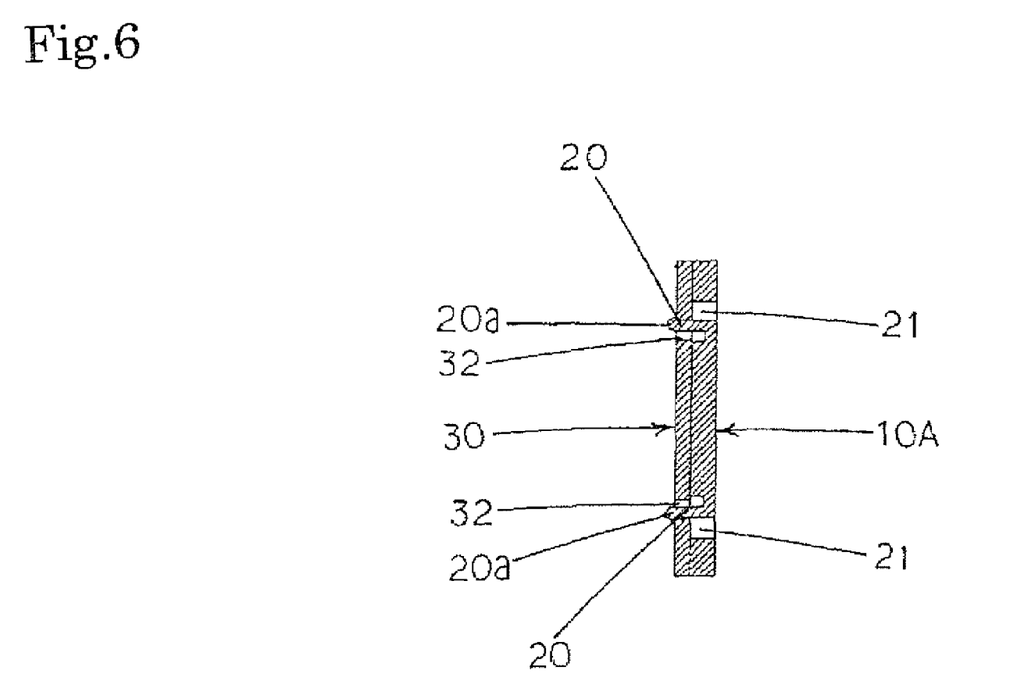
FIG. 6 shows a cross-sectional view taken along the line C-C in FIG. 5(a).

A plan view of the cell counting board wherein the cover plate 30 is attached to the main body 10A is shown in FIG. 5(a), its partially broken front view is shown in FIG. 5(b), and a cross-sectional view taken along the line C-C in FIG. 5(a) is shown in FIG. 6.

The attachment of the cover plate 30 to the main body 10A can be performed only by engaging the projection sections 20 of the main body 10A to the engagement holes 32 of the cover plate 30. In this case, the insertion of the projection section 20 to the engagement hole 30 is easily performed because of the moderate elasticity of the projection section 20. After the insertion, the hook-shaped leading edge section 20a of the projection section 20 engages the edge of the engagement hole 32 elastically, so that the cover plate 30 is securely fixed to the main body 10A without positional gap.

In this attachment condition, the upper face of the part 11 of the main body 10A is close relation with the lower face of the cover plate 30, thereby a space 40 of the predetermined distance (0.1 mm) is formed between the upper face of the part 11 of the main body 10A and the lower face of the cover plate 30 [FIG. 5(b)]. In order to perform the cell counting by use of this cell counting board, diluted blood or cell suspension may be injected from a part of the lands 12, 13, which appears from the cutout portions 31 of the cover plate 30, into the space 40 with a pipette chip or the like.

In this cell counting board, the attachment of the cover plate 30 to the main body 30 can be performed only by engaging the engagement holes 32 of the cover plate 30 to the projection sections 20 of the main body 10A. So, assembly processing is easy. Furthermore, a space 40 of the predetermined distance between the upper face of the lands 12, 13 of the main body 10A and the lower face of the cover plate 30 is formed only by engaging the cover plate 30 to the main body 10A. So, it does not take much trouble to keep the accuracy of distance of the space 40. For these reasons, this cell counting board can be mass-produced at extremely low costs. This cell counting board has superior characteristics for convenience, not only because it is suitable for disposable from a view point that it can be mass-produced at extremely low costs and from a view point of the biohazard and the like, and also because it is a simple structure where the engagement holes 32 of the cover plate 30 are engaged to the projection sections 20 of the main body 10A.

In this cell counting board, both the main body 10A and the cover plate 30 are made of synthetic resin. So, if highly precise mold for molding is prepared, it is capable to mass-produce at extremely low costs the cell counting board which has high quality, and is good for the accurate distance of the space 40 after attachment of the main body and the cover plate to one another.

Figure 7A:
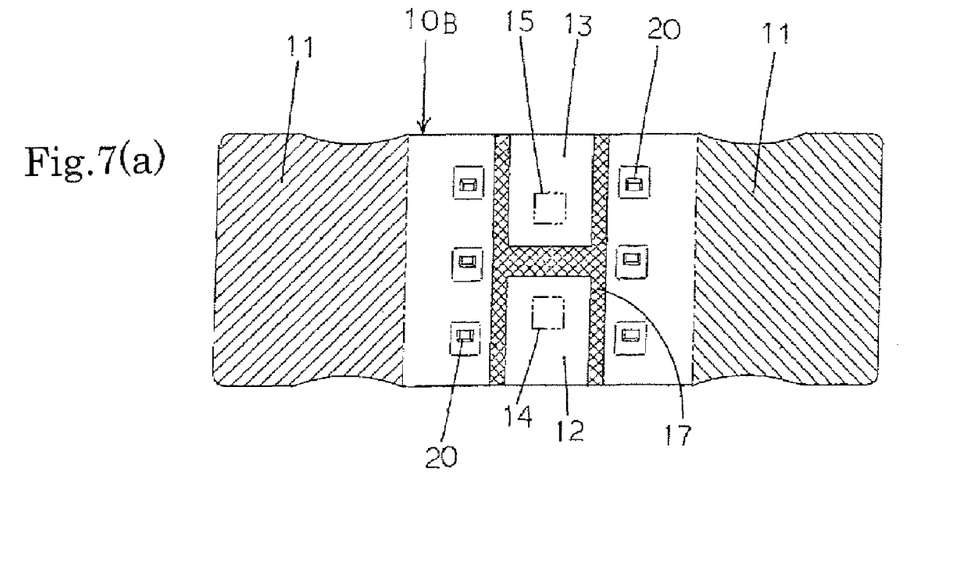
FIG. 7(a) shows a plan view of the main body of the cell counting board related to another embodiment.
Figure 7B:
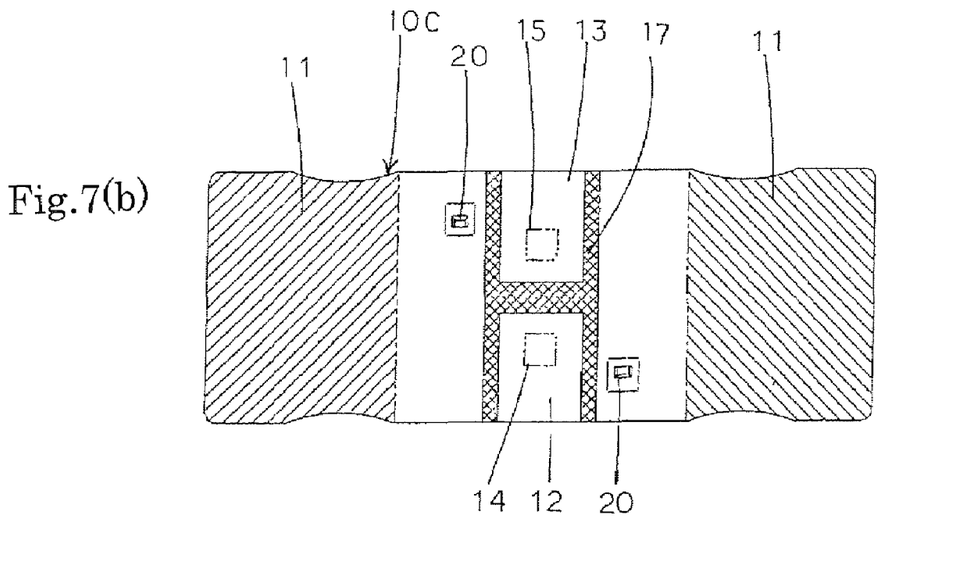
FIG. 7(b) shows a plan view of the main body of the cell counting board related to another different embodiment.
Figure 8:
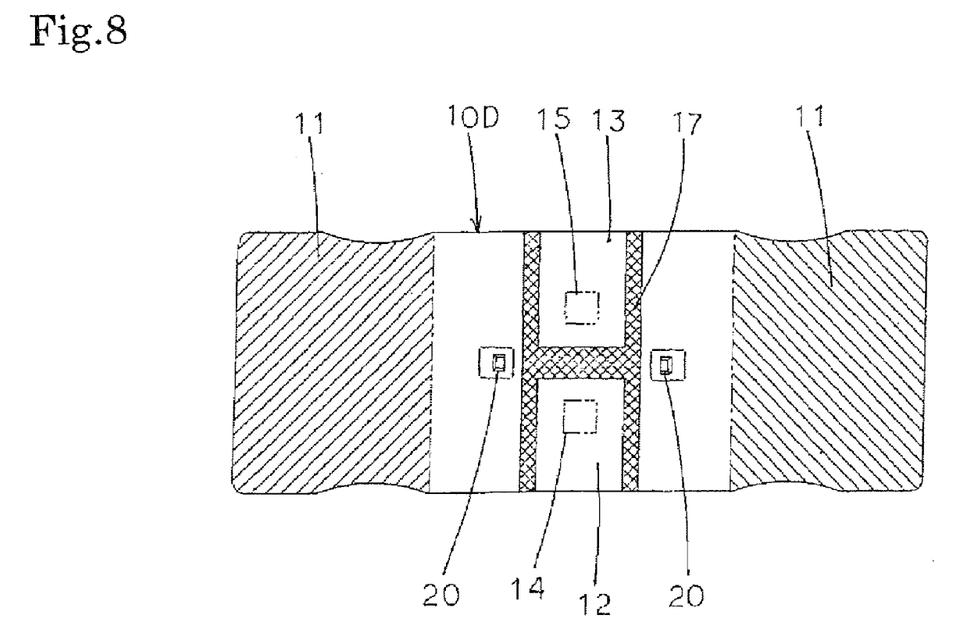
FIG. 8 shows a plan view of the main body of the cell counting board related to another different embodiment.

And, the cell counting board of the above embodiment is just an example, and is possible for many variation. For example, while the number of the projection sections 20 of the main body 10A is four in the above cell counting board, six projection sections 20 are provided with the main body 10B shown in FIG. 7(a), and two projection sections 20 are diagonally provided with the main body 10C shown in FIG. 7(b), and two projection sections 20 are provided toe to toe with the main body 10D shown in FIG. 8. The cover plate 30 is securely fixed to the main body 10 without positional gap, provided at least two projection sections 20 as shown in FIG. 7(b) and FIG. 8. Of course, the position and the number of the engagement holes 32 are set up depending on the position and the number of the projection sections 20 of the main body 10 (B~D).

Figure 9A:
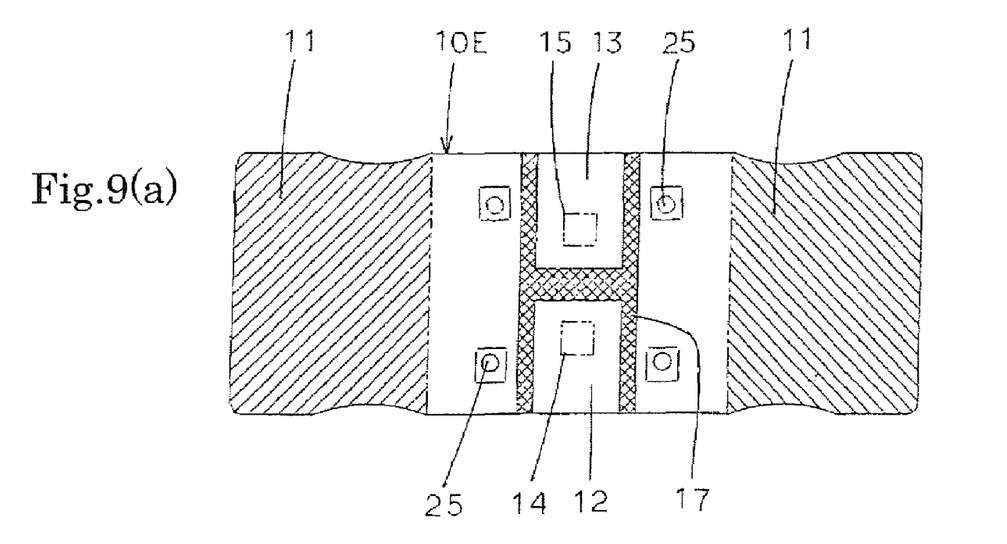
FIG. 9(a) shows a plan view of the main body of the cell counting board related to another different embodiment.
Figure 9B:
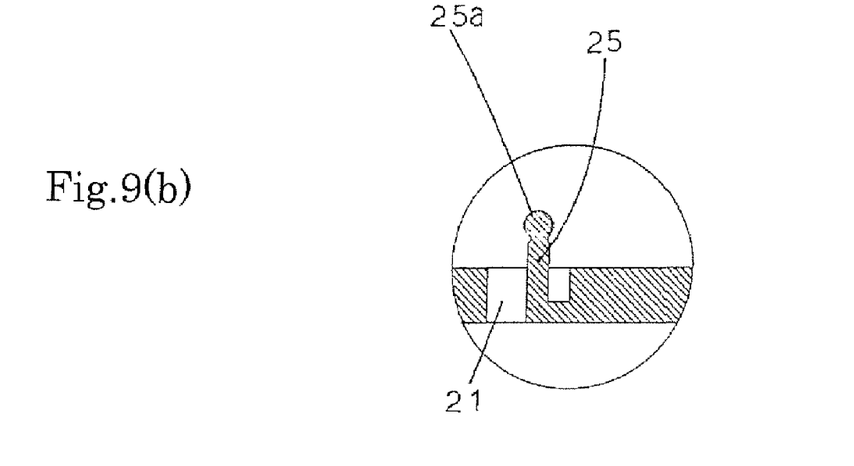
FIG. 9(b) shows an enlarged cross sectional view of its projection section.

Furthermore, while the projection section 20 of the main body 10A in the above cell counting board has rectangular parallelepiped shape, the projection section 25 of the main body 10E shown in FIG. 9 has a columnar shape, and the leading edge section 25a has a spherical shape. Depending on this, though not shown in the figures, the engagement hole of the cover plate 30 is formed circularly. In this case, the cover plate 30 is attached to the main body 10E by engaging the spherical leading edge section 25a of the projection section 25 to the circular engagement hole.

Figure 10A:
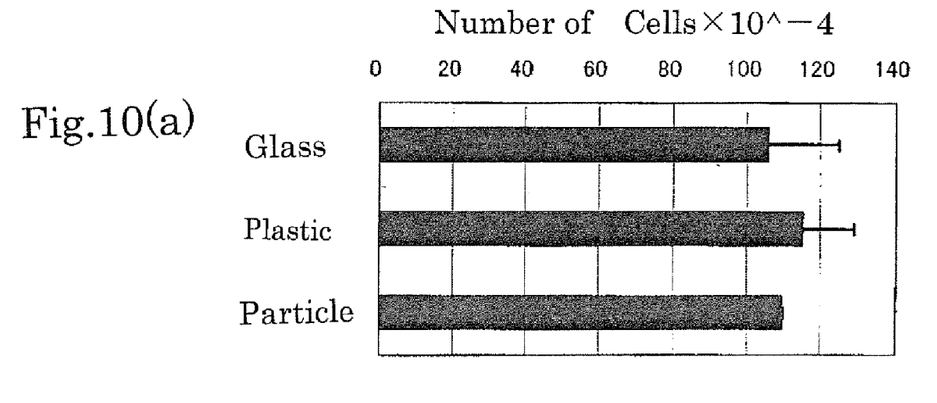
FIG. 10(a) shows comparison of result of the cell counting in cultured CHO-K1 cells.

Next, an experimental example which was performed using the above plastic cell counter board for cultured cells and erythrocytes. After chinese hamster ovary cells (CHO cells) were cultured in DMEM/F-12 media, they were washed with PBS (phosphate buffered 0.15 M physiological saline) solution, and detached with 0.25% trypsin EDTA enzyme solution to prepare isolated cells. The above cells were sedimented by centrifugation at 1,500_rpm for 5 minutes, and then suspended in DMEM media containing 10% serum. An equal amount volume of this cell suspension and trypan blue staining solution were mixed, and the aliquot of the mixture was injected into the cell inlet (space 40 in the above cell counter board). Cells were observed with a phase-contrast reverse microscope. FIG. 10(a) shows the practical result in which cell numbers were counted.

In FIG. 10(a), "Glass" indicates the result of cell counting using a glass-made conventional hemocytometer of Burker-Turk type, "Plastic" indicates the result of cell counting using the above cell counter board, and "Particle" indicates the result of cell counting using a cell counting apparatus (a particle counter) (Beckman Coulter, Inc., Z1 counter). Cell counting was performed after trypan blue staining except for cell counting with a particle counter. Here, closed bars indicate average cell numbers of counting (counting number N=4-6), and the line bars indicate the standard error of the average. As clearly shown in this FIG. 10(a), the result of the cell counting with the above cell counter board exhibited to be equivalent to that with conventional products.

Next, erythrocytes from human peripheral blood were measured. To PBS solution containing heparin was added a drop of blood drawn from peripheral blood. This was diluted further with PBS solution, and the aliquot of the mixture was injected into the cell inlet (space 40 in the above cell counter board). Similarly, the cells were measured with a glass-made hemocytometer. The results of the cell counting are shown in FIGS. 10(b), and 10(c).

Figure 10B:
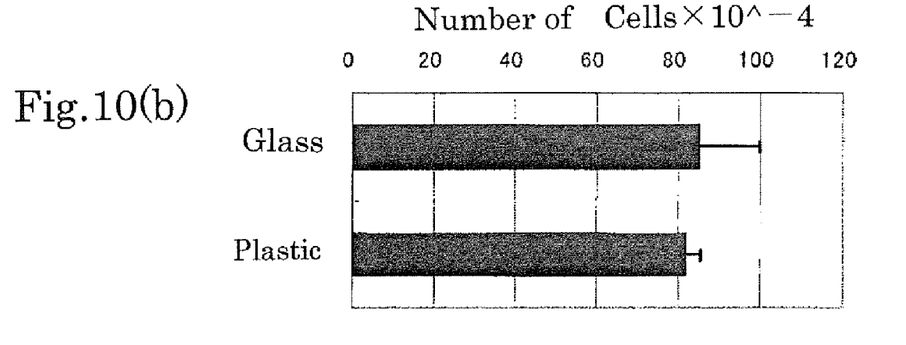
FIGS. 10(b), and 10(c) show comparison of result of the cell counting in human peripheral erythrocytes.
Figure 10C:
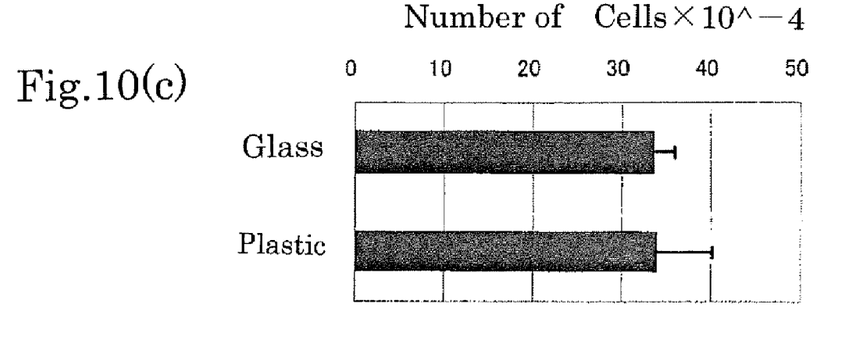

In FIGS. 10(b), and 10(c), "Glass" indicates the result of cell counting using a glass-made conventional hemocytometer of Burker-Turk type, "Plastic" indicates the result of cell counting using the above cell counter board. Here, measurement in FIG. 10(b) was performed under non-staining and measurement in FIG. 10(c) was performed after trypan blue staining. In both FIG. 10(b) and FIG. 10(c), closed bars indicate average cell numbers of counting (counting number N=4-6), and the line bars indicate the standard error of the average. As clearly shown in these FIGS. 10(b), and 10(c), the result of the cell counting with the above cell counter board exhibited to be equivalent to that with conventional products.

What is claimed is:

1. A cell counting board comprising:
   a main body; and
   a cover plate attached to the main body;
   wherein the main body comprises a planar land section positioned at a lower position by a predetermined distance with respect to the top face of the main body, a counting section for counting cells provided at the land section, and at least two projection sections for positioning and fixing the cover plate on the land section, the projection section being provided in the vicinity of the land section,
   the cover plate has engagement holes formed at locations thereof, the location corresponding to the projection of the main body, and
   wherein a space of the predetermined distance is generated between the top face of the land section of the main body and the bottom face of the cover plate, when the cover plate is attached to the main body by engaging each of the projection sections of the main body with the corresponding engagement hole of the cover plate.

2. A cell counting board as set forth in claim 1, wherein the main body and the cover plate are made of synthetic resin.

3. A cell counting board as set forth in claim 2, wherein the projection sections of the main body are disposed in one side and in the other side with respect to the land section, and the number of the projection sections disposed in the one side is two, and the number of the projection sections disposed in the other side is two.

4. A cell counting board as set forth in claim 2, wherein the projection section of the main body has rectangular parallelepiped shape having a hook shaped leading edge section.

5. A cell counting board as set forth in claim 1, wherein the projection sections of the main body are disposed in one side and in the other side with respect to the land section, and the number of the projection sections disposed in the one side is two, and the number of the projection sections disposed in the other side is two.

6. A cell counting board as set forth in claim 5, wherein the projection section of the main body has rectangular parallelepiped shape having a hook shaped leading edge section.

7. A cell counting board as set forth in claim 1, wherein the projection section of the main body has rectangular parallelepiped shape having a hook shaped leading edge section.

* * * * *